US010064395B2

(12) United States Patent
Chapa (10) Patent No.: US 10,064,395 B2
(45) Date of Patent: Sep. 4, 2018

(54) BEEHIVE MONITORING SYSTEM (71) Applicant: Mario Chapa, Montegomery, TX (US)

(72) Inventor: Mario Chapa, Montegomery, TX (US)

(*) Notice: Subject to any disclaimer, the term of this patent is extended or adjusted under 35 U.S.C. 154(b) by 0 days.

(21) Appl. No.: 14/858,887

(22) Filed: Sep. 18, 2015

(65) Prior Publication Data
US 2017/0079249 A1 Mar. 23, 2017

(51) Int. Cl.
A01K 47/06 (2006.01)
G01N 19/10 (2006.01)
G01G 19/52 (2006.01)
G01J 1/42 (2006.01)
G06F 3/16 (2006.01)

(52) U.S. Cl.
CPC ............ A01K 47/06 (2013.01); G01G 19/52 (2013.01); G01J 1/42 (2013.01); G01N 19/10 (2013.01); G06F 3/16 (2013.01)

(58) Field of Classification Search
CPC ..... A01K 47/06; A01K 29/005; H04W 52/04; H04N 7/183; G08C 17/02; G01N 19/10; G01G 19/52; G01J 1/42; G06F 3/16
See application file for complete search history.

(56) References Cited

U.S. PATENT DOCUMENTS 3,994,034 A * 11/1976 Van Damme .......... A01K 47/06
449/12
4,346,490 A * 8/1982 Katz .................... B01D 1/2887
449/2
2004/0077290 A1 * 4/2004 Bromenshenk ........ A01K 15/02
449/3
2007/0224913 A1 * 9/2007 Brisson .................. A01K 51/00
449/3
2010/0062683 A1 * 3/2010 Brundage .............. A01K 47/06
449/1
2012/0077413 A1 * 3/2012 Engel ..................... A01K 47/06
449/50
2012/0295514 A1 * 11/2012 Keppens ................ A01K 47/06
449/13
2015/0049919 A1 * 2/2015 Humal ................... A01K 47/06
382/110

(Continued)

FOREIGN PATENT DOCUMENTS

WO  WO 2015185899 A1 * 12/2015 ............ A01K 47/06

Primary Examiner — An T Nguyen
(74) Attorney, Agent, or Firm — William C. Yarbrough, III; Kearney, McWilliams & Davis, PLLC (57) ABSTRACT The present application includes a system configured to monitor and track the health and productivity of a beehive. Information associated with environmental conditions around the beehive are monitored along with conditions inside the beehive. This information is processed through a control system and compared to baseline expected values. Communication data is transmitted by the control system to a remote device to notify the beekeeper of the present and past health and productivity of the beehive. The beekeeper may remotely operate one or more functions to affect the beehive. Additionally, an electronic monitoring device is used to track the number of bees that leave and enter the beehive. A dual-gate design is used to determine the direction of travel of each bee so as to determine a more accurate reflection of the health of the beehive.

21 Claims, 3 Drawing Sheets (56) References Cited

U.S. PATENT DOCUMENTS

| | | | |
|---|---|---|---|
| 2015/0084784 A1* | 3/2015 | Suta | H04Q 9/02 340/870.01 |
| 2015/0123801 A1* | 5/2015 | de Leon | A01K 47/06 340/573.3 |
| 2015/0366169 A1* | 12/2015 | Jiang | A01K 29/005 449/20 |
| 2017/0079249 A1* | 3/2017 | Chapa | A01K 47/06 |

* cited by examiner

BEEHIVE MONITORING SYSTEM

BACKGROUND

1. Field of the Invention

The present application relates generally to bee equipment and, more particularly, to a system for monitoring the status, activity, and health of a beehive.

2. Description of Related Art

Beekeeping is the maintenance of honey bee colonies. The bees are kept in order to collect their honey and other products that the hive naturally produces to pollinate crops. Another use of raising bees is to sell hives to other beekeepers. Beehive production is affected by a number of different factors. Some factors that may affect production of the bees are temperature within the hive, humidity, and illnesses. It is important to be able to monitor and regulate the controllable factors within the beehive to ensure optimal production.

Different types of products have been developed to assist in monitoring hives. Typically monitoring is done by physical inspection of the hive. A beekeeper visually views the hive and assesses the amount of production that has taken place. Physical inspection has a disadvantage of only granting a snap shot in time or a present condition. It is difficult to fully grasp the development of issues or problems with isolated inspections.

Another method that has been used is to attempt to count the bees within the hive by using a sensor. These have several limitations including only being able to count the passage of a bee through a certain point. Direction of the bee is not tracked or determined. Bee production can be greatly linked to bee population.

Another disadvantage of present beekeeping activities is the difficulty of passive beekeepers to adequately monitor the hive. A large portion of the world lives in urban cities not ideal for the keeping of hives. Therefore, those that do keep a hive often place them at a remote location. The distance between the urban beekeeper and the hive creates a hurdle that limits the ability of the urban beekeeper in properly maintaining the hive.

Although some strides have been made in assisting a beekeeper in properly and adequately monitoring the hive, considerable shortcomings remain. It is desirable to provide a beehive monitoring system configured to make remote location beekeeping more effective and properly communicate the health and status of a hive to the beekeeper.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The system in accordance with the present application overcomes one or more of the above-discussed problems commonly associated with conventional beehive monitoring devices. Specifically, the system of the present application is configured to track through one or more sensors ambient conditions and physical characteristics of the beehive. The system also is configured to monitor the activity level of the bees. This information is processed by a control system and compared to baseline data for the generation of health and productivity notifications. The notifications are provided to the beekeeper for his/her use in maintaining the beehive. The beekeeper may receive communication remotely or via a message center on the monitoring device. The beekeeper may control or operate various features of the system to affect ambient conditions at the beehive. These and other unique features of the system are discussed below and illustrated in the accompanying drawings.

The system will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

The beehive monitoring system of the present application is illustrated in the associated drawings. The system includes a monitoring device located adjacent to a beehive and configured to collect input data regarding the health and productivity of a beehive. The monitoring device has one or more ambient sensors configured to collect ambient data around the beehive, one or more gates configured to track the movement of individual bees into and out of the beehive in the form of movement data, and a control system in communication with the one or more sensors and the one or more gates. The control system is configured to process the movement data and the ambient data (input data) to generate communication data for review by the beekeeper. The control system configured to transmit communication data to the beekeeper regarding the health and productivity of the beehive.

Figure 1:
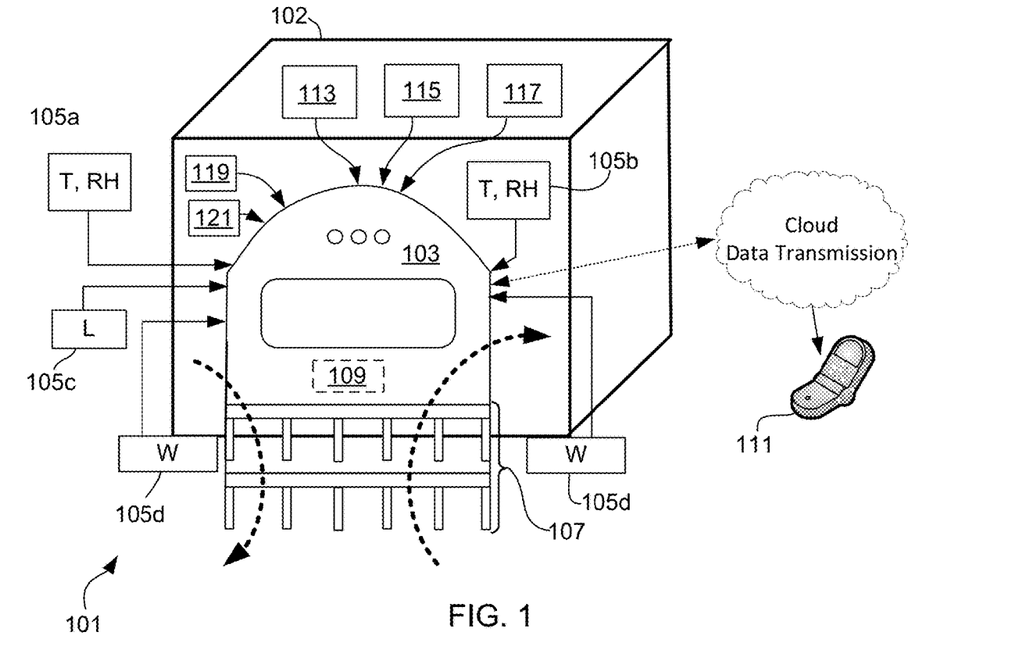
FIG. 1 is a chart of a beehive monitoring system according to the preferred embodiment of the present application.

Referring now to the drawings wherein like reference characters identify corresponding or similar elements in form and function throughout the several views. FIG. 1 in the drawings illustrate a chart of a beehive monitoring system 101 according to the preferred embodiment of the present application. System 101 is resting next to beehive 102, such that as bees leave and enter beehive 102, the bees must pass through a portion of system 101. System 101 includes a monitoring device 103 having one or more sensors 105, one or more gates 107, and a control system 109 (see FIG. 6). System 101 is configured to obtain and relay information regarding beehive 102 and the bees to a beekeeper to ensure proper maintenance, health, and production.

Sensors 105 are used by system 101 to monitor various external or physical properties of beehive 102. For example, sensors 105 may include sensors configured to measure temperature, light, and weight. Ambient sensors are those sensors dedicated to obtaining information related to the surrounding area or environment to beehive 102. The ambient sensors may obtain information related to the external ambient environment or internal ambient environment to beehive 102. Sensors 105a and 105b are ambient sensors. Sensor 105a is configured to obtain at least one of temperature and/or relative humidity readings from the environment. Sensor 105b is similar in form and function to that of sensor 105a except that it is obtaining the same or similar information within beehive 102. Additionally, sensor 105c is a light sensor. Sensor 105c is configured to measure the amount of light around beehive 102. It is understood that sensor 105c (or an additional sensor) may be located internally to beehive 102 to measure the amount of light within beehive 102. Weight sensor 105d is located beneath a portion of beehive 102 and is configured to provide weight data to control system 109. By monitoring the weight of beehive 102, a beekeeper is able to determine when it is time to visit the hive and remove some of its byproducts (i.e. honey . . . ).

Sensors 105 are useful in system 101 because they are configured to provide important information related to beehive 102. Beehive 102 is affected in a number of ways by its environment. By monitoring the environment, proper care for beehive 102 may be performed. It is understood that many different factors can affect bees in their production rates. For example: temperature, relative humidity, time of year, number of bees, and so forth. By properly monitoring this information, a beekeeper is better prepared to properly maintain the beehive.

Information gathered through sensors 105 are compiled and processed by control system 109. This information is relayed to the beekeeper. This information helps him/her to take proper action and identify issues promptly. Some examples of actions to take based on information gathered by sensors 105 are as follows. The temperature within beehive 102 should be fairly stable throughout the year. In winter months, if the temperature in beehive 102 is below where it should be, this is an indication of the bees starving or freezing. A beekeeper may elect to feed the bees or provide some degree of warmth. If the temperature is higher than where it should be in warmer months than that is an indication that the bees are spending more time than usual in an effort to cool the hive and therefore production falls. A beekeeper may elect to increase circulation in the hive to assist in cooling it down.

Gates 107 are used to count or track the number of bees entering and leaving beehive 102. Control system 109 is configured to store an approximate number of bees within beehive 102, therefore a proper count of bees may be maintained throughout the day. Bees have different jobs within a hive. Some leave and return, some help the queen, other bees stay and guard the hive. By monitoring the number of bees that leave and enter beehive 102, a beekeeper is able to monitor the health and production of the hive. This information is useful because it can serve as a guide to the beekeeper as to when to split the hive. It may represent that there are more than one queen in the hive if the population is increasing at higher than expected rates. It may provide an indication of illness if the population is decreasing at higher than expected rates. Additionally, use of gates 107 help to identify where the losses are coming from (i.e. tracking how many that left the hive actually returned). Losses may be realized by having a parasite of some type within beehive 102. Knowing the number of bees and their activity level, a beekeeper is able to take necessary actions to remedy the situation.

As alluded to, control system 109 is configured to compare data received (ambient sensor data, weight sensor data, . . . ) through sensors 105 to that of one or more corresponding baseline data in order to ascertain the health and productivity of the beehive. The beekeeper is able to set such preset baseline data into control system 109 and make necessary adjustments.

Figure 2:
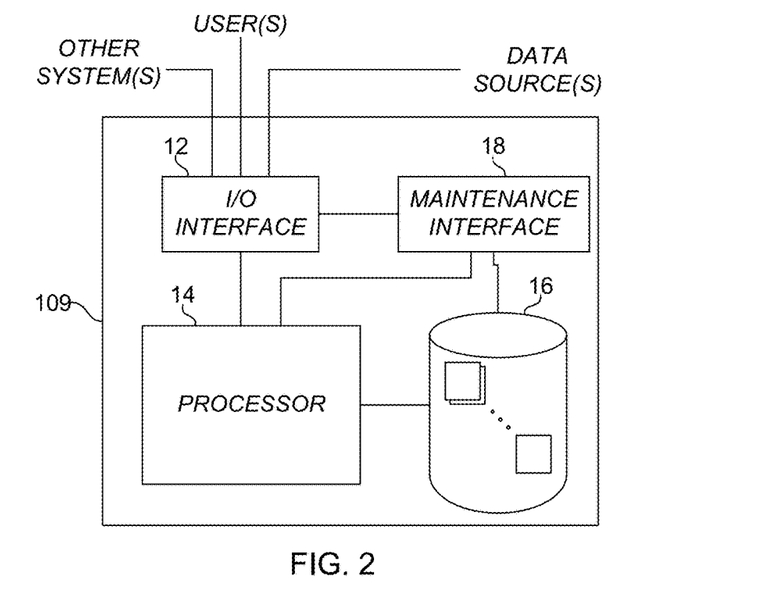
FIG. 2 is a schematic of an exemplary electronic control system within the beehive monitoring system of FIG. 1.

Referring now also to FIG. 2 in the drawings, control system 109 is configured to receive and process data from sensors 105, compare that data with one or more corresponding baseline data, and generate selectively tailored notification data for reception by the beekeeper.

The control system 109 includes an input/output (I/O) interface 12, a processor 14, a database 16, and a maintenance interface 18. Alternative embodiments can combine or distribute the input/output (I/O) interface 12, optimization engine 14, database 16, and maintenance interface 18 as desired. Embodiments of control system 109 can include one or more computers that include one or more processors and memories configured for performing tasks described herein below. This can include, for example, a computer having a central processing unit (CPU) and non-volatile memory that stores software instructions for instructing the CPU to perform at least some of the tasks described herein. This can also include, for example, two or more computers that are in communication via a computer network, where one or more of the computers includes a CPU and non-volatile memory, and one or more of the computer's non-volatile memory stores software instructions for instructing any of the CPU(s) to perform any of the tasks described herein. Thus, while the exemplary embodiment is described in terms of a discrete machine, it should be appreciated that this description is non-limiting, and that the present description applies equally to numerous other arrangements involving one or more machines performing tasks distributed in any way among the one or more machines. It should also be appreciated that such machines need not be dedicated to performing tasks described herein, but instead can be multi-purpose machines, for example smart phones, electronic tablets, and computer workstations, that are suitable for also performing other tasks. Furthermore the computers and machines may use transitory and non-transitory forms of computer-readable media. Non-transitory computer-readable media is to be interpreted to comprise all computer-readable media, with the sole exception of being a transitory, propagating signal.

The I/O interface 12 provides a communication link between external users, systems, and data sources and components of control system 109. The I/O interface 12 can be configured for allowing one or more users to input information to control system 109 via any known input device, such as display 113. Examples can include a keyboard, mouse, touch screen, microphone, and/or any other desired input device. The I/O interface 12 can be configured for allowing one or more users to receive information output from control system 109 via any known output device. Examples can include a display monitor, a printer, a speaker, and/or any other desired output device. The I/O interface 12 can be configured for allowing other systems to communicate with control system 109. For example, the I/O interface 12 can allow one or more remote computers to access information, input information, and/or remotely instruct control system 109 to perform one or more of the tasks described herein. The I/O interface 12 can be configured for allowing communication with one or more remote data sources, such as device 111. For example, the I/O interface 12 can allow device 111 to receive communication data to produce notifications, graphical performance data, and health data, transmitted by one or more ways, including: fax, text, email, cloud based upload/download (i.e. world-wide web), to name a few. The communication data may be viewed and modified via I/O interface 12 to adjust format, presentation, and structure of the data as provided to the beekeeper.

The database 16 provides persistent data storage for control system 109. While the term "database" is primarily used, a memory or other suitable data storage arrangement may provide the functionality of the database 16. In alternative embodiments, the database 16 can be integral to or separate from control system 109 and can operate on one or more computers. The database 16 preferably provides non-volatile data storage for any information suitable to support the operation of control system 109. Database 16 stores information used in the generation of communication data. Examples may include, tabular scientific data, formatting data, equations, client information, checklists, registration data, unit conversions, and so forth.

The maintenance interface 18 is configured to allow users to maintain desired operation of control system 109. In some embodiments, the maintenance interface 18 can be configured to allow for reviewing and/or revising the data stored in the database 16 and/or performing any suitable administrative tasks commonly associated with database management. This can include, for example, updating database management software, revising security settings, and/or performing data backup operations. In some embodiments, the maintenance interface 18 can be configured to allow for maintenance of processor 14 and/or the I/O interface 12. This can include, for example, software updates and/or administrative tasks such as security management and/or adjustment of certain tolerance settings.

The processor 14 is configured to receive the electrical signal data 111 and generate performance data representative and particular to a specific A/C system. Processor 14 may access and compare information stored on database 16 for producing such performance data. Processor 14 can include various combinations of one or more processors, memories, and software components.

Some functions of control system 109 allow the user to not only view performance characteristics of the beehive but also provide command data to the control system in order to affect the health and productivity of the beehive itself. Beekeeper may provide command data to control system 109 through device 111 or may do it manually at the beehive. Device 111 is remotely located to beehive 102 and may be typically thought of as a portable electronic device or type of computer (desktop or laptop for example). Ideally device 111 is carried by the beekeeper. The communication data is provided by the control system wirelessly. It is understood that other embodiments may permit for communication data to be received via direct wire transfer (USB or memory cards). Where done wirelessly, communication data is transferred through the internet. Command data may likewise be provided to control system 109 through device 111. Device 111 is configured to have a selected user interface for the display of notifications, graphical representations, and providing of command data. The user interface may be that of a mobile application.

System 101 may further include one or more devices that may be used by the beekeeper to affect the health and productivity of beehive 102. System 101 may further include a heater 113 configured to selectively regulate the temperature within beehive 102. Heater 113 may be automatically operated or manually operated through the control of device 111. Heater 113 is used to ensure the temperature of beehive 102 does not drop below a predetermined temperature.

System 101 may further include a skylight vent 115 configured to selectively adjust the amount of light permitted to enter into beehive 102. As stated previously, certain parasites may enter beehive 102 and harm the bees. Some of these parasites are susceptible to certain levels of light. A beekeeper may elect to adjust the amount of light into beehive 102 to affect the health and productivity of the beehive.

System 101 may further include a microphone 117 configured to record the sound of the bees within the beehive. The control system 109 is configured to transmit sound data to the beekeeper to listen to on device 111 or at device 103. The microphone can help the beekeeper know how much effort is being made by the bees to cool the hive in warmer months. More time spent cooling the hive means less productivity.

From microphone 117, the beekeeper may elect to control a ventilator 119. System 101 may further include a ventilator 119 used to increase the air flow within beehive 102. This may be a fan or a number of vents and may be operated to increase the amount of airflow within the hive.

Additionally, system 101 may further include a camera 121 in communication with the control system 109. Control system 109 is configured to transmit video data to the beekeeper for viewing on a device, such as device 111. Visual images from within beehive 102 can assist the beekeeper in possibly interpreting the notifications he/she receives and provide an additional level of confirmation.

It is understood that the beekeeper may operate each of these additional optional components 113, 115, 117, 119, and 121 via device 111, through device 103, or manually at the beehive.

Referring now also to FIGS. 3-6 in the drawings, electronic monitoring device 103 is illustrated in greater detail. Device 103 is configured to house control system 109 and provide selected notifications and health or productivity information to the beekeeper. Sensors 105 and components 113, 115, 117, 119, and 121 may operatively communicate with control system 109 via wired or wireless methods. Where wires are used, device 103 includes an aperture 123 for the passage of wires. Aperture 123 is angled such that the exterior opening is lower than the internal opening on device 103. This helps to prevent water or other environmental elements from entering within device 103. Although not necessary, this design for aperture 123 is preferred.

Device 103 further includes a message center 125. Message center is optional, but preferred. Message center 125 is configured to relay notification information in a visual format to a beekeeper at beehive 102. The notification information is similar to that seen on device 111. The information is related to the health and productivity of the bees.

Figure 3:
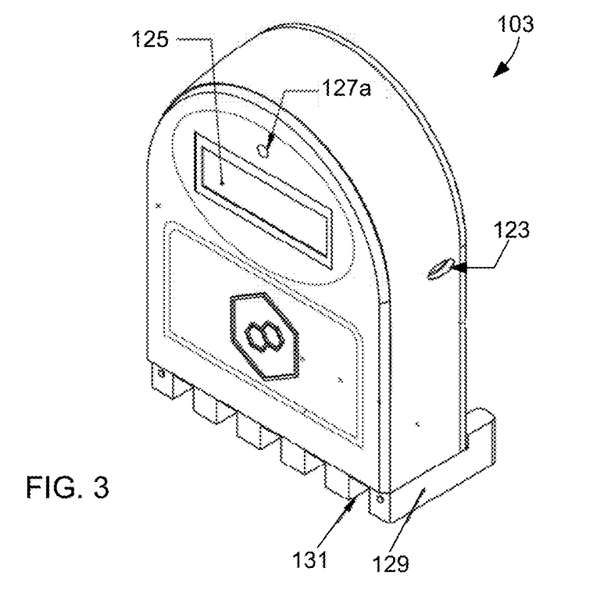
FIG. 3 is a perspective view of the beehive monitoring device as seen in FIG. 1.

Additionally, device 103 may further include a light display 127. Display 127 is configured to provide a visual color coded indication of the status of beehive 102. This allows the beekeeper to determine from a distance away from device 103 whether any actions need to be performed. As seen in FIG. 3, display 127a is a single light. The light may be various colors, each relaying a particular meaning. For example, yellow may mean control system 109 has determined a potential problem when comparing the current and past data to the baseline data. The color green may relay that everything is operating correctly and that no action is required. A blue color may convey the need to take a particular action that is not of a particular danger (i.e. a suggestion). For example it may mean that the beekeeper should split the hive as control system 109 compares the population of the bees. Again, it may mean that the beekeeper should collect honey. Other colors and their respective meanings may be used.

Figure 4:
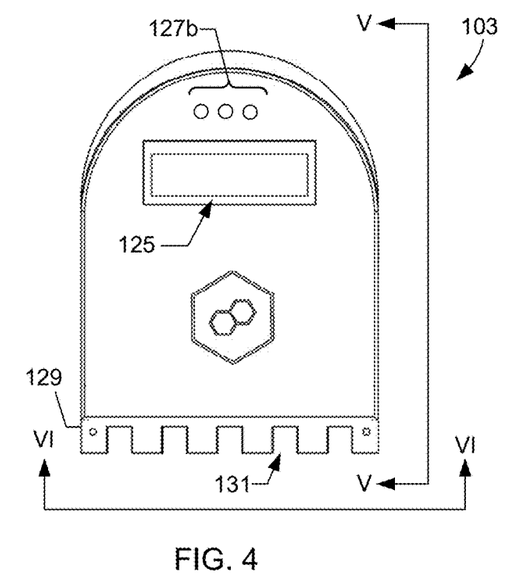
FIG. 4 is a front view of the beehive monitoring device of FIG. 3.
Figure 5:
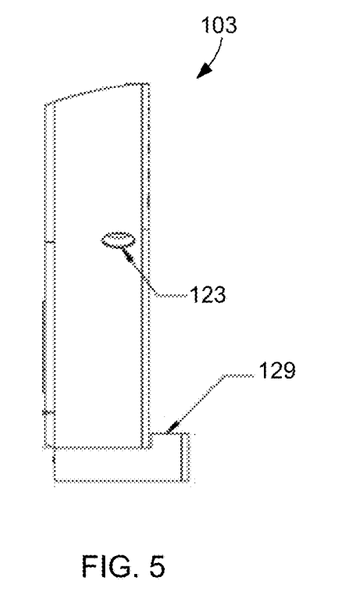
FIG. 5 is a side view of the beehive monitoring device of FIG. 4.

As seen in FIG. 4, display 127b is shown as having three lights, each of which has an independent color associated with it. Display 127b is similar in form and function to that of display 127a except for the number of lights. The lights can be assigned a single color or multiple colors. Additionally, in display 127b, different messages can be conveyed by the combination of colors displayed (i.e. green and yellow together).

As noted previously, device 103 includes gates 107. Device 103 is located adjacent to a portion of beehive 102 wherein a base portion 129 of device 103 directs the bees to pass through one or more gates 107. Base 129 extends behind device 103 to permit base 129 to actually enter into the hive. Base 129 is configured to stabilize device 103 and system 101. Gates 107 are in communication with base 129 and are configured to track the passage of bees entering and leaving beehive 102. A number of passages 131 are provided in base 129.

Figure 6:
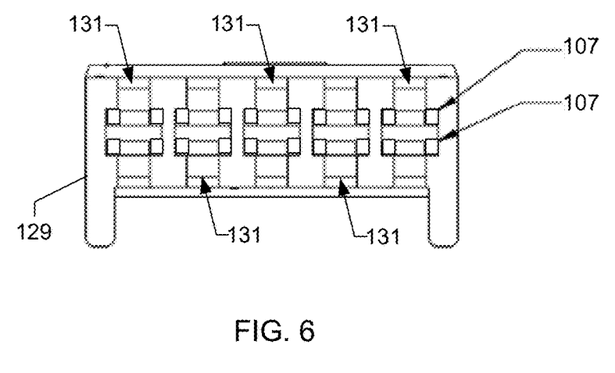
FIG. 6 is a bottom view of the beehive monitoring device of FIG. 5.

As seen in FIG. 6, each passage includes at least one gate 107. Gate 107 is any type of sensor that enables control system 109 to track the passage of a bee from one location to another. Common types of gates 107 are those that rely on a light interrupter or a magnetic field sensor, where passage of a bee interrupts a signal or light. Where one gate 107 is used, control system 109 is able to determine a bee passed through the gate but is unable to determine which direction the bee was going. By using two gates 107 in each passage 131, control system 109 is able to determine the direction of the bee. This allows control system 109 to know the number of bees that left the hive and that returned to the hive at any given time. This information is very useful in determining the cause of losses in population in the hive. Where a bee only trips a single gate or fails to fully pass through both gates will not register as fully passing through into or out of beehive 102.

Figure 7:
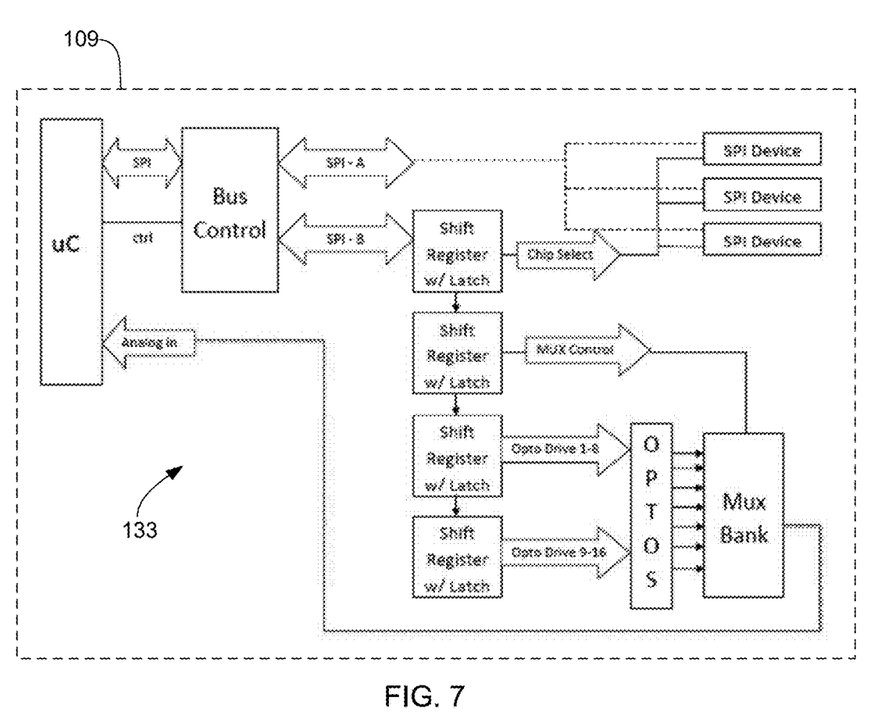
FIG. 7 is a schematic of an exemplary processor in the electronic control system of FIG. 2 in operation with the beehive monitoring device of FIG. 2.

Referring now also to FIG. 7 in the drawings, a schematic of an exemplary processor 133 in control system 109. It is understood that the operations, layout, and interrelations of the various components may vary depending on the precise functions selected.

It is understood that the term beekeeper refers to anyone involved in the care and/or maintenance of a beehive.

The current application has many advantages over the prior art including at least the following: (1) an ability to relay health and productivity information to a beekeeper at a remote location so as to increase the efficiency of the beekeeper; (2) the ability to more quickly spot and cure dangers that arise that may threaten the beehive; (3) increase the ability to have urban beekeepers that can now live remotely to the beehive; (4) remote control of the beehive; and (5) ability to track the direction of the bees as they pass through the gate(s).

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A beehive monitoring system, comprising:
   a monitoring device in communication with a beehive and configured to collect input data regarding the health and productivity of a beehive, the monitoring device located external to the beehive for the recordation and transmittal of qualitative and quantitative information related to the health and productivity of the beehive, the monitoring device having:
   one or more ambient sensors configured to collect ambient data around the beehive;
   a base defining one or more passages for the movement of a bee, each passage includes a plurality of gates configured to track the number and movement of individual bees into and out of the beehive in the form of number and movement data, the plurality of gates within each passage are situated side-by-side, centrally within the passage, each of the plurality of gates includes a plurality of light interrupter sensors located directly across from other, at 180 degrees, on opposing sides of the passage, at an area internally within the passage, the plurality of passages remaining outside the beehive, wherein movement through one gate of the plurality of gates within a passage selectively trips at least one light interrupter sensor, the order and timing in which one or more of the plurality of sensors are tripped are utilized to determine the number and movement data of bees; and a control system in communication with the one or more of the plurality of light interrupter sensors and the one or more of the plurality of gates, the control system configured to process the number and movement data of the bees and the ambient data to generate qualitative and quantitative data, the control system configured to transmit qualitative and quantitative data to the beekeeper regarding the health and productivity of the beehive.

2. The beehive monitoring system of claim 1, wherein the one or more ambient sensor is configured to measure temperature inside the beehive.

3. The beehive monitoring system of claim 1, wherein the one or more ambient sensor configured to measure temperature outside the beehive.

4. The beehive monitoring system of claim 1, wherein the one or more ambient sensor is configured to measure the relative humidity.

5. The beehive monitoring system of claim 1, wherein the one or more ambient sensor is configured to measure the amount of light outside the beehive.

6. The beehive monitoring system of claim 1, further comprising:
a weight sensor in communication with the control system to provide weight data.

7. The beehive monitoring system of claim 1, wherein the control system is configured to compare data received through the one or more ambient sensors and light interrupter sensors to that of one or more baseline data in order to ascertain the health and productivity of the beehive.

8. The beehive monitoring system of claim 1, wherein the communication data provided by the control system is wirelessly transmitted to a remote electronic device.

9. The beehive monitoring system of claim 1, further comprising:
a remote electronic configured to receive the communication data from the control system, the beekeeper monitoring the remote electronic device for notifications related to the health and productivity of the beehive.

10. The beehive monitoring system of claim 1, wherein the beekeeper is able to provide command data to the control system in order to affect the health and productivity of the beehive.

11. The beehive monitoring system of claim 10, wherein the beekeeper is able to affect the health and productivity of the beehive by adjusting the amount of light within the beehive.

12. The beehive monitoring system of claim 10, wherein the beekeeper is able to affect the health and productivity of the beehive by adjusting the temperature within the beehive.

13. The beehive monitoring system of claim 1, further comprising:
a heater configured to selectively heat the interior of the beehive, the heater operated through the control system.

14. The beehive monitoring system of claim 1, further comprising:
a skylight vent configured to selectively adjust the amount of light permitted into the beehive.

15. The beehive monitoring system of claim 1, further comprising:
a microphone configured to record the sound of the bees within the beehive, the control system configured to transmit sound data to the beekeeper to listen to.

16. The beehive monitoring system of claim 1, further comprising:
a ventilator in communication with the control system, the ventilator configured to move air within the beehive.

17. The beehive monitoring system of claim 1, further comprising:
a camera in communication with the control system, the control system configured to transmit video data to the beekeeper for viewing.

18. The beehive monitoring system of claim 1, further comprising:
a color coded light display configured to provide the beekeeper a visual notification of the status of the beehive.

19. The beehive monitoring system of claim 1, further comprising:
a message center configured to relay visual information regarding the present health and productivity of the beehive to the beekeeper.

20. The beehive monitoring system of claim 1, wherein the control system is configured to produce and transmit graphical representations of the health and productivity of the beehive.

21. The beehive monitoring system of claim 1, wherein the plurality of light interrupter sensors located directly across from each other are used in tandem, positioned at 180 degrees, on opposing sides of the passage, at an area internally with within the passage, the plurality of passages remaining outside the beehive, wherein passage movement through the one gate of the plurality of gates the gate within a passage selectively trips at least two light interrupter sensors, the order and timing in which one or more of the plurality of sensors are tripped help to are utilized to determine the number and movement data of bees.

* * * * *

UNITED STATES PATENT AND TRADEMARK OFFICE
CERTIFICATE OF CORRECTION

PATENT NO. : 10,064,395 B2
APPLICATION NO. : 14/858887
DATED : September 4, 2018
INVENTOR(S) : Mario Chapa It is certified that error appears in the above-identified patent and that said Letters Patent is hereby corrected as shown below:

On the Title Page

Item Nos. (71) and (72) - "Montegomery, TX" should be changed to "Montgomery, TX"

In the Claims

Column 9, Line 6 - "directly across from other," should be changed to "directly across from each other,"

Column 10, Line 50 - "internally with within the passage" should be changed to "internally within the passage"

Column 10, Line 52 - "the plurality of gates the gate within" should be changed to "the plurality of gates, the gate within"

Column 10, Line 53 - "a passage selectively trips" should be changed to "a passage, selectively trips"

Column 10, Line 55 - "are tripped help to are utilized to" should be changed to "are tripped help to, are utilized to,"

Signed and Sealed this
Twenty-ninth Day of January, 2019

Andrei Iancu
*Director of the United States Patent and Trademark Office*